United States Patent [19]
Dickakian

[11] Patent Number: 4,762,797
[45] Date of Patent: Aug. 9, 1988

[54] METHOD FOR DETERMINING THE FOULING TENDENCY OF HYDROCARBONS

[75] Inventor: Ghazi B. Dickakian, Kingwood, Tex.

[73] Assignee: Exxon Chemical Patents Inc., Linden, N.J.

[21] Appl. No.: 849,600

[22] Filed: Apr. 8, 1986

[51] Int. Cl.$^4$ .................. G01N 30/00; G01N 33/28
[52] U.S. Cl. .................. 436/60; 73/61.1 C; 73/61.2; 73/64; 436/161
[58] Field of Search .................. 436/2, 140, 141, 161, 436/162, 60, 139; 73/61.2, 61.1 C, 64

[56] References Cited

U.S. PATENT DOCUMENTS

| | | | |
|---|---|---|---|
| 1,756,981 | 5/1930 | Jurrissen | 208/309 |
| 2,196,989 | 4/1940 | Henry et al. | 208/309 |
| 3,049,964 | 8/1962 | Miller et al. | 356/70 |
| 4,634,680 | 1/1987 | Kingsley | 436/161 |
| 4,671,103 | 6/1987 | Dickakian | 210/656 X |

FOREIGN PATENT DOCUMENTS 0455272 4/1975 U.S.S.R. .................. 73/64

OTHER PUBLICATIONS

Magaril et al., Khimiya i Tekhnologiya Topliu: Masel, No. 3, pp. 15–16, 1970.
Poirier et al., Chem. Abstracts, vol. 100, 1983, No. 100:36717m.

Primary Examiner—Barry S. Richman
Assistant Examiner—Robert J. Hill, Jr.
Attorney, Agent, or Firm—J. F. Hunt

[57] ABSTRACT

A method for easily and quickly determining the tendency of a petroleum fraction (oil or resid) to foul in refinery equipment comprises determining the ratio of the saturates or aromatics (polar, neutral or total): asphaltenes for the petroleum in question and comparing this ratio with a plot of ratios and fouling tendencies for a set of prior oils or resids. It has been found that the ratio and the relationship to fouling are completely consistent and reproducible phenomenon which thereby provide a rapid means for a substantially quantitative measure of fouling tendency.

15 Claims, 2 Drawing Sheets

METHOD FOR DETERMINING THE FOULING TENDENCY OF HYDROCARBONS

BACKGROUND OF THE INVENTION

1. Field of the Invention

The present invention relates to a method for determining the tendency of petroleum fractions e.g., crudes and residues, to foul heated metal surfaces such as heat exchangers.

2. Related Art

Different crude oils have different precipitating and fouling characteristics with regard to heated oil refinery surfaces. The problem of predicting the offending substances in a particular crude il which foul heat exchanger equipment in oil refineries and petrochemical plants has been virtually unresolved. Fouling of hydrocarbon streams, consisting of carbonaceous deposits on heat exchanger surfaces, leads to a blockage of flow and a decrease in heat transfer. Both resulting conditions severely reduce efficiency in the processing of the crude oil. If it can be predicted which fractions of the crude oils are troublesome, measures can be taken in advance to prevent this fouling by either removing the offending substances causing the deleterious deposits, or by adding antifouling additives to the flow stream to reduce deposit formation. Therefore, it would be most desirable to be able to predict these fouling substances.

There are a number of methods available for determining the rates of fouling of hydrocarbon streams. Conceptually, they are all similar in that they attempt to measure the change in heat transferred from a heated surface to a test fluid.

One approach is to use a test unit which is configured to allow measurement of the fluid temperature at the exit of the heat exchanger while the metal temperature of the heated tube is controlled, which is generally referred to as the Thermal Fouling Tester (TFT). This configuration provides for close simulation of refinery and petrochemical plant heat exchanger operations and provides for measurement of the significant effect of fouling which is indicated by the reduction of heat transfer. The test unit provides for a thermal fouling evaluation of the crude oil in an accelerated test which is designed to reproduce the fouling problem experienced in a refinery over several months. Acceleration is provided by carrying out test operating temperatures higher than those in a particular refinery unit, so that the prospective level of fouling can be produced in a reasonable period of time (usually 3-4 hours). Heat transfer data is obtained by holding the heater tube at a constant temperature, while measuring the change in the liquid outlet temperature. As fouling progresses, i.e., a carbonaceous deposit build up on the heater tube surface, a decrease in the fluid outlet temperature results when using a constant outlet liquid temperature operation. The change in liquid outlet temperature with time provides the basic heat data required for comparative evaluation of untreated material and additive-treated material. The rate of change in outlet liquid temperature versus time shows relative fouling tendencies. The duration of this test is usually three hours or longer. In practice in the laboratory, the turnaround for a single sample in this equipment is about one man day to obtain results. And one test unit will generally produce about 200 tests in a year. However, refinery feeds and streams change constantly and multiple tests, e.g., 10 to 50 or 60 per day may be required for full evaluation and control of the refinery operations.

Tests have shown that in fouling crude oils, the saturates fractions are generally in excess of 75 wt. % of the total crude and its aromatic fractions tend to be less than 25 wt. % of such fouling crude oils, which provided at least an empirical measure of determining the tendency of various petroleum fractions to foul.

Crude oils, being fluids can be fractionated into three separate and specific components: a hydrocarbon saturate fraction; a neutral hydrocarbon aromatic fraction; and a third fraction comprising aromatic components containing sulfur, oxygen and nitrogen (polar aromatic fraction).

Liquid chromatography is used to separate and quantify the aforementioned fractions in crude oils or other oils and petroleum fractions that are characterized by a tendency to foul refinery equipment. When these fractions are compared with the fractions similarly obtained from nonfouling crude oils, the substances causing fouling were identified. The fouling characteristics of crude oils or other petroleum fluids is measured by determining quantitively the composition of the petroleum fluid by techniques well known in the art such as Liquid Chromatography. The petroleum fluid is separated quantitively into three previously identified specific fractions, i.e.; a hydrocarbon saturate fraction, a neutral hydrocarbon aromatic fraction and a third fraction comprising the aromatic fraction containing sulfur, oxygen and nitrogen (polar aromatic fraction). The amount of neutral aromatics and polar aromatics present in the hydrocarbon fluid gives valuable information to predict the fouling tendency of the fluid to be tested.

It is an advantage of the present invention that a rapidly performable and quantitative method for determining the fouling tendency of a petroleum fraction is provided. Hence there is provided a method of predicting the fouling which results from the refinery treatment of any given petroleum stream. These and other advantages and features of the present invention will become clear from the following description.

SUMMARY OF THE INVENTION

Briefly, the invention concerns the discovery that ratio of saturates (total saturates), polar aromatics, neutral aromatics or total aromatics (polar+neutral) to asphaltenes in a petroleum fraction provides an accurate measure of the tendency of said petroleum fraction to foul exposed heated metal surfaces, e.g., in processing equipment. In the preferred embodiment the total aromatics are employed.

In the case of the aromatic (neutral, polar or total):asphaltenes the higher the ratio, the lower the fouling tendency. For example a petroleum stream having a ratio as defined which is above about 20 would be very low fouling. Generally a ratio of from 0.1 to 19 would indicate high fouling material.

In order to obtain the relationship between the ratio of aromatics:asphaltenes and fouling tendency, a plurality of petroleum oils or resids can be evaluated to determine their fouling tendency and the ratio of aromatics:asphaltenes for each may be conveniently plotted to provide a standard curve, chart or the like. Hence, some of the points for determining the fouling tendency at a given ratio may be interpolated between actual determinations. Any subsequent petroleum fraction then need only have the ratio determined and the fouling tendency determined from the standard curve, chart or the like.

One aspect of the present invention is a method for determining the tendency of a petroleum fraction to foul exposed heated metal surfaces comprising determining the amounts of polar aromatics, neutral aromatics or total aromatics in said petroleum fraction, determining the amount of asphaltenes in said hydrocarbon, calculating the ratio of said amounts of polar aromatics, neutral aromatics or total aromatics to asphaltenes and comparing said ratio to a previously determined tendency to foul for a petroleum fraction with the same ratio.

Alternatively the ratio of saturates to $C_7$-asphaltenes may be calculated and similarly compared to a previously determined tendency to foul for a petroleum fraction with the same ratio. It would be appreciated that since the $C_7$-asphaltenes are less soluble in saturates, that low ratios would indicate low fouling, i.e., the opposite of the meaning of the aromatic:$C_7$-asphaltene ratio.

The specific methods of determining fouling tendency or the ratio of aromatics or saturates:asphaltenes are not critical, so long as they are reliable and reproducible.

The term "petroleum fraction" as used herein includes crude oils, petroleum residues, hydrocarbons, heteroatom compounds normally found as constituents in crude oils and the fractions derived from any of the above.

DETAILED DESCRIPTION OF THE INVENTION

The present Fouling Index method is useful for determining the fouling (or the rate of carbonaceous deposit formation) in a variety of hydrocarbons derived from petroleum, for example: crude oil, crude oil distillate fraction, crude oil residues, heat transfer oils and lubricating base oils.

The concentrations of components of petroleum which are commonly associated with fouling may be determined by any method which is reliable and reproducible.

Generally speaking, High Performance Liquid Chromatography (HPLC) was used in regard to the present invention to separate and measure various fractions of deasphaltenated crude oils or resids. HPLC is fully described in a book by L. R. Snyder, et al. entitled "Introduction to Modern Liquid Chromatography".

HPLC separates successfully deasphaltenated crude oils into the three fractions that are the key in determining the crude composition. These fractions are: a saturate fraction, a neutral aromatic fraction, and a polar aromatic fraction. The repeatability of the HPLC composition analysis is very good. Duplicate tests made on two crudes showed very good agreement.

HPLC systems are available in hundreds of different configurations from the basic, low cost single pump system to fully automated multi-solvent gradient systems.

The separations by HPLC are accomplished by pumping solvent/sample through a column which is packed with materials optimized for efficient separations. Separation results from differences in the extent to which the various components in the mixture interact with the column packing material. If there is little or no interaction, the component(s) will be passed quickly through the column packing resulting in decreasing elution time. Each component elutes from the column at a slightly different time, where it is detected and collected.

A basic HPLC unit is composed of a mobile phase reservoir, a pump for solvent delivery, and a sample injector. A chromatography efficiency HPLC separation is achieved by using a combination of correct column, good LC apparatus, good operation and specialized know-how.

Petroleum oils, such as crude oils and heavy hydrocarbons, are composed of two major parts; high molecular weight asphaltene (fraction insoluble in paraffinic solvents) and a lower molecular weight asphaltene-free oil. The asphaltene and the oil fraction vary significantly in their chemical structure, coking characteristics, thermal characteristics, average molecular weight and distribution. The following Table 1 illustrates the varying differences in the characteristics of a typical heavy oil, its asphaltene and deasphaltenated oil fractions:

TABLE 1

|  | Crude Oil | Deasphaltenated Oil | Asphaltene |
|---|---|---|---|
| Average mol. wt. | 190 | — | 1150 |
| Coke yield (%) @ 450° C. | 5-12 | — | 20-30 |
| Carbon/Hydrogen ratio | 0.52 | 0.47 | 0.59 |
| Melting point (°C.) | liquid | liquid | 190 |
| Oxygen content (wt %) | 0.38 | 0.34 | 1.86 |

Figure 1:
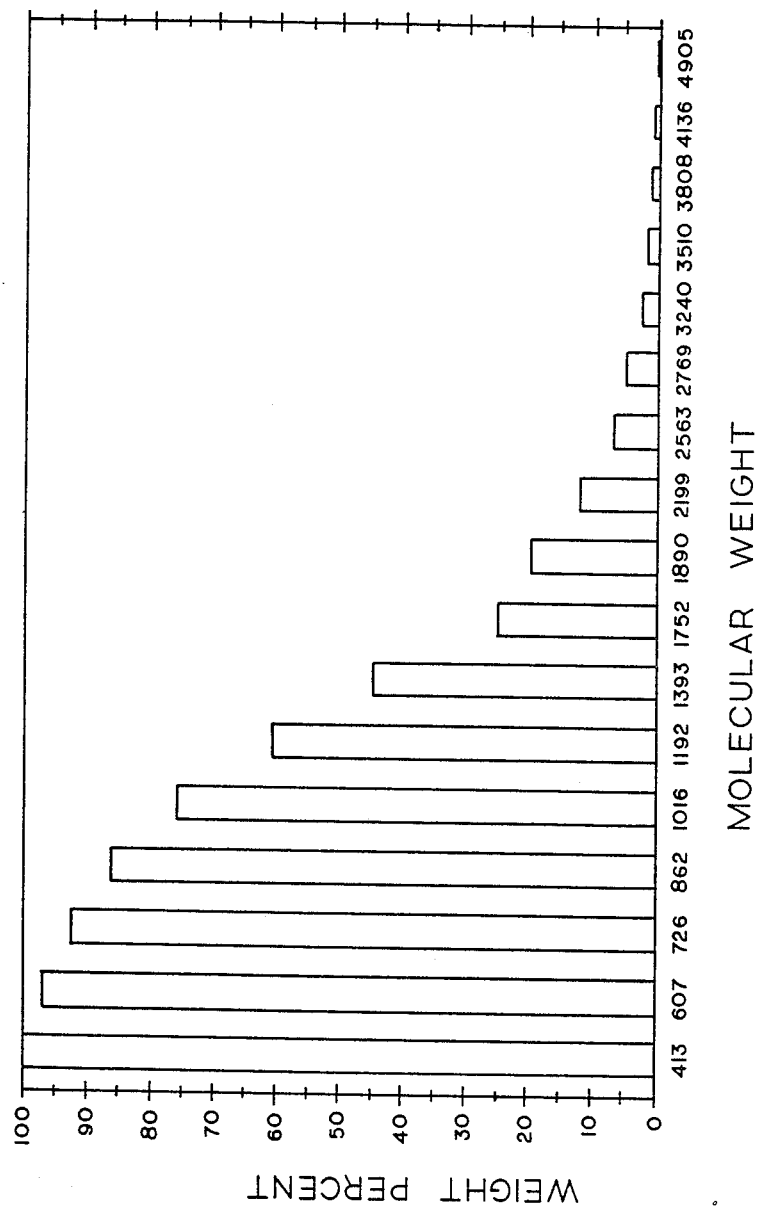
FIG. 1 is a bar graph showing the gel permeation chromatography (GPC) molecular weight percentile of n-heptane insolubles ($C_7$-asphaltenes) (Mn=1178) found in a representative crude oil.

Asphaltenes present in heavy oils have high molecular weight and very broad molecular weight distribution, sometimes with molecular weights up to 10,000. A typical molecular weight distribution of a crude is illustrated in FIG. 1. It has been found that fouling is primarily a compatibility problem of asphaltenes (defined herein as n-heptane insolubles or $C_7$-asphaltenes) with the other components of the oil. Hence, since asphaltenes are soluble in aromatics but generally insoluble in the saturated hydrocarbons, it is a discovery of this invention that the amount of aromatics relative to asphaltenes determines the compatibility. Thus the type of oil is not of overall significance, e.g., crude, residual or otherwise. Hence, the aromatics:asphaltenes as described above and the comparable fouling associated with the ratio in question may be determined on an actual crude or resid or on synthetic compositions. Subsequently petroleum oils of any nature may have their aromatic/asphaltene ratio determined directly from the prior data. For example, FIGS. 2 and 3 were prepared from numerous different oils of different grade classifications and the two curves are essentially the same. Thus it is not so much the relative amounts of saturates and aromatics but only the relative amount of aromatics and asphaltenes which controls and determines compatibility and hence fouling.

Typical neutral aromatics include for example, indanes, naphthenonaphthalenes and naphthenophenanthenes. Typical polar aromatics include for example, benzothiophenes, indenothiophenes, acenaphthylenothiophenes, benzofurans, indenobenzofurans and acenaphthylenofurans.

The asphaltenes may be determined by insolubilization with antisolvents such as paraffinic solvents such as n-pentane, n-hexane, cyclohexane, isopentane, petroleum ether, n-heptane and the like. Paraffinic and polar asphaltene antisolvents can be used and these are effective over a broad range of oil/solvent ratios. These antisolvents should be of low molecular weight, low viscosity and have low boiling characteristics to allow easy separation and recovery of the insolubles (asphaltenes).

The paraffin antisolvents include $C_3$–$C_{20}$ paraffins. The paraffin antisolvents are preferably up to $C_{10}$ straight or branched alkanes, usually $C_5$ to $C_{10}$, e.g., suitable antisolvents include pentane, isopentane, hexane, 2-methyl hexane, n-heptane, octane, nonane, decane, isooctane and the like.

The polar antisolvents cover a broader spectrum of materials. The present polar solvents are organic compounds which are liquids under the conditions of use. The term "polar" refers to atoms such as oxygen, sulfur, oxygen halogens and nitrogen. A partial listing of suitable polar antisolvents includes alcohols such as, isobutanol, 2-pentanol, isoamyl alcohol; ketones such as acetone; methyl ethyl ketone; ethers such as diethyl ether, methyl propyl ether; esters such as methyl formate, butyl formate, methyl acetate, methyl propionate; glycol ethers, such as ethylene glycol monomethyl ether, ethylene glycol diethyl ether; heteroatom compounds such as furan, tetrahydrofuran, furfural, methyl pyridine, and the like. Mixtures of hydrocarbon and polar materials are desired antisolvents for petroleum streams containing functional groups. Sufficient antisolvent is used to insolubilize the asphaltenes, generally about 1:10 to 1:100 (volume) sample to antisolvent. In the present examples n-heptane was the solvent used to deasphaltenize the petroleum fraction. The asphaltene was determined by dissolving the total oil sample in n-heptane at a ratio of 1:40 at room temperature and filtering through 0.35 micron fluorcarbon membrane. If desired asphaltenes extraction with the antisolvents can be made at higher temperature, e.g., 30°–100° C. Analytical methods other than liquid extraction with antisolvent can also be used for determining asphaltenes for example; clay-silica gel chromatography and light scattering.

EXAMPLES

All of the Examples cited herein demonstrating the fouling characteristics of crude and residual oils utilized a laboratory test apparatus known as the Thermal Fouling Tester.

The Tester is a modification of the Alcor Jet Fuel Oxidation Tester described in ASTM Vol. 50 D-3241. It is configured to allow measurement of the fluid temperature at the exit of the heat exchanger while the metal temperature of the heated tube is controlled. The test thus measures the change in temperature of a fluid which has been pumped across a heated surface. The outlet temperature is directly related to the heat transferred to the fluid. If fouling occurs, a deposit adheres to the heated surface and insulates the surface from the test fluid. The insulating deposit reduces the rate of heat transfer to the fluid and its temperature decreases. The rate of change in the fluid temperature is a measure of the rate of fouling. The time over which temperature measurements are recorded was set at 3 hours.

The following Examples are reported for illustrative purposes only and are not to be construed as limiting the invention herein described.

Unless specified otherwise, as used herein, all parts and percentages are by weight and based on the total weight of the oil.

Fouling Measurement of Oils by Thermal Fouling Tester

The fouling characteristics ($\Delta T$) of the specified oils used in this investigation were measured by the thermal fouling tester using the following operation conditions:

| | |
|---|---|
| Type of heater tube | Two piece C/S tube |
| Metal temperature (°F.) | 700 |
| Oil Circulation rate (cc/Min) | 3.0 |
| Preheating (°F.) | 70 |
| Pressure (psig) | 500 |
| Time (hours) | 3.0 |

Composition of Oils by HPLC

In the analytical separation, a 3.9 mm by 30 cm long ENERGY ANALYSIS COLUMN commercially available from Waters Associates, 34 Maple Street, Milford, Mass. 01757, USA, was used with n-heptane as the solvent and mobile phase. The samples were "dissolved" in the n-heptane at a volume ratio of 1:40 of sample:solvent. The solution was filtered through a 0.45 micron fluorocarbon membrane filter to remove any insoluble material (asphaltenes).

The deasphaltenated "oil" was then injected into the ENERGY ANALYSIS COLUMN. The first peak was the saturates:normal, iso and cyclosaturates. Any aliphatic unsaturates are eluted at this time. The neutral aromatics, up through six condensed rings, eluted as the next fraction. At this point, the mobile phase was reversed through the column. This was done by the use of a high pressure valve activated by timed events. With the flow in the reverse direction the polar aromatics eluted. This fraction contained sulfur, nitrogen and oxygen-containing aromatics. The total instrument time was 23 minutes.

The neutral aromatics, and polar aromatics were determined from the chromatographic area, times the response factor calculated from the API gravity. The removal of "asphaltenes" was done quantitatively by filtration, and the saturates were determined by difference.

The analytical separation was done on a dual detector instrument (UV at 254 nm and differential refractometer in series). The column was a 3.9 mm by 30 cm long ENERGY ANALYSIS COLUMN. The solvent and mobile phase was n-heptane.

The flow rate was maintained at 2.0 ml/min at room temperature. The instrument also contained a high pressure valve used in column backflush. The valve was activated from timed events on an M-730 Data Module.

Asphaltene Determination

The sample was dissolved in n-heptane at a ratio of 1:40 (0.5 grams of sample dissolved in 20 ml of n-heptane) and mixed using ultrasonic bath for 30 minutes at room temperature. This solution was filtered through a tared 0.35 micron fluorcarbon membrane filter. After the filter was dried, it was re-weighed for the amount of saturates and asphaltenes.

In these examples the "Fouling Index" is the ratio of total aromatics:n-heptane insolubles.

EXAMPLE 1

Sixteen different crude oils were evaluated for fouling characteristics (TFT, $\Delta T°$ F.) and analyzed (HPLC and insolubles). The ratio of total aromatics:$C_7$-asphaltenes (n-heptane) and related fouling is reported in TABLE II. The ratio is reported under the heading Fouling Index (FI). The higher the FI the less incompatibility and hence less fouling.

TABLE II

Relation of Incompatibility to TFT - Fouling

| Crude No. | Fouling Index | TFT - Fouling ($\Delta$ T, °F.) |
| --- | --- | --- |
| 1 | 6.1 | 60, 61 |
| 2 | 2.5 | 56 |
| 3 | 10.2 | 39, 40, 41 |
| 4 | 5.1 | 49 |
| 5 | 73.1 | 00.0 |
| 6 | 11.0 | 50 |
| 7 | 4.1 | 41 |
| 8 | 3.9 | 45 |
| 9 | 3.5 | 82, 77 |
| 10 | 31.2 | 0 |
| 11 | 13.8 | 25 |
| 12 | 19.2 | 5 |
| 13 | 5.2 | 80 |
| 14 | 3.5 | 81 |
| 15 | 3.7 | 77 |
| 16 | 29 | 0, 4 |

Figure 2:
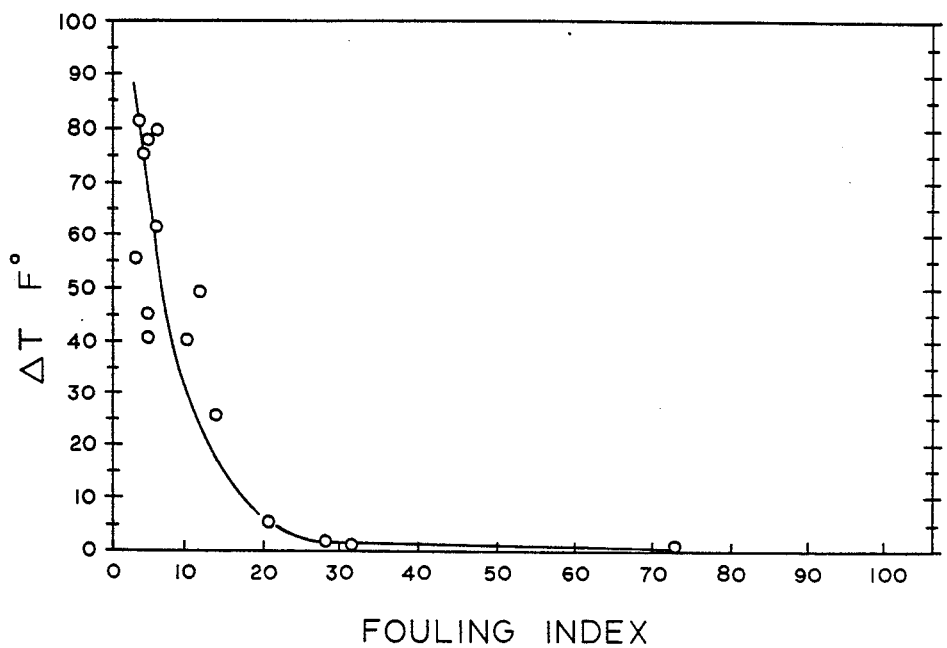
FIG. 2 is a graph based on evaluation of several crude oils showing the relationship between fouling as determined by the Thermal Fouling Tester and the ratio of total aromatics:$C_7$-asphaltenes.
Figure 3:
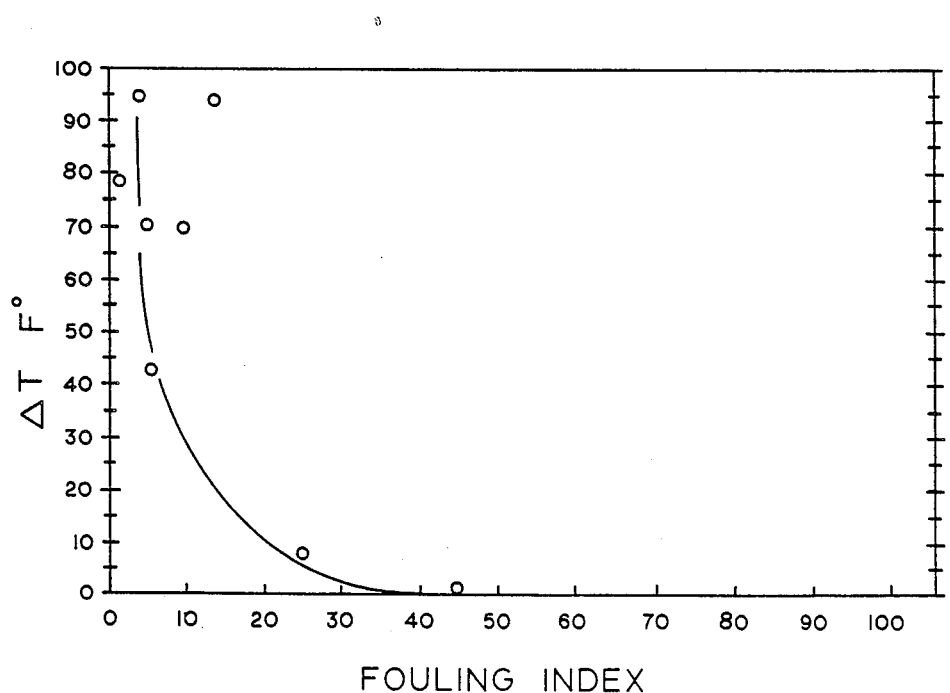
FIG. 3 is a graph based on evaluation of several petroleum resids showing the relationship between fouling as determined by the Thermal Fouling Tester and the ratio of total aromatics:$C_7$-asphaltenes.

This data is also graphically represented in FIG. 2.

EXAMPLE 2

Ten different petroleum resides were evaluated for fouling characteristics (TFT $\Delta F°F$. ) and analyzed (HPLC and insolubles). The ratio of total aromatics:C7-asphaltenes (n-heptane) and the related fouling for each resid is reported in TABLE II. The higher FI the lower the fouling. The results in TABLE III are reported in FIG. 3.

TABLE III

Relation of Incompatibility to TFT - Fouling

| Resid No. | Fouling Index | TFT - Fouling ($\Delta$ T, °F.)* |
| --- | --- | --- |
| 1 | 10.4 | 60 (900° F.) |
| 2 | 8.0 | — |
| 3 | 44 | 0 (950° F.) |
| 4 | 4.0 | 55 (900° F.) |
| 5 | 25.8 | 8 (900° F.) |
| 6 | 5.8 | 42 (900° F.) |
| 7 | 4.3 | 53 (900° F.)/94 (990° F.) |
| 8 | 0.9 | 79 (950° F.) |
| 9 | 1.0 | — |
| 10 | 14.1 | 95 (950° F.) |

*( ) numbers are for the metal heater temperature in the Thermal Fouling Tester.

The invention claimed is:

1. A method for determining the tendency of a sample petroleum fraction to foul exposed heated metal surfaces comprising:
   (a) determining the amount of saturates or aromatics in said sample petroleum fraction;
   (b) determining the amount of asphaltenes in said sample petproleum fraction;
   (c) calculating the ratio of saturates or aromatics in said sample petroleum fraction to asphaltenes in said sample petroleum fraction from the amounts determined in steps (a) and (b); and
   (d) comparing said ratio to a previously determined tendency to foul exposed heated metal surfaces for a prior petroleum fraction having substantially the same ratio as said sample petroleum fraction to determine the tendency of said sample petorleum fraction to foul exposed heated metal surfaces.

2. The method according to claim 1 wherein the determining step (b) comprises determining the amount of $C_7$-asphaltenes in the sample petroleum fraction and the calculating step (c) comprises calculating the ratio of total aromatics in said sample petroleum fraction to $C_7$-asphaltenes in said sample petroleum fraction.

3. The method according to claim 1 wherein the determining step (b) comprises determining the amount of $C_7$-asphaltenes in the sample petoleum fraction and the calculating step (c) comprises calculating the ratio of saturates in said sample petroleum fraction to $C_7$-asphaltenes in said sample petroleum fraction.

4. The method according to claim 1 wherein step (a) comprises determining the amount of total aromatics in said sample petroleum fraction by reverse phase high performance liquid chromatographytechnique.

5. The method according to claim 4 wherein said sample petroleum fraction is deasphaltenated and the amount of total aromatics is determined on the deasphlatenated sample petroleum fraction.

6. The method according to claim 5 wherein said sample petroleum fraction is deasphaltenated by contacting said sample petroleum fraction with an insolubilizing amount of an antisolvent for asphaltenes and recovering asphaltenes.

7. The method according to claim 1 wherein the previously determined tendency to foul exposed heated metal surfaces of step (d) is determined by the steps of:
   (e) determining the amount of total aromatics for as plurality of prior petroleum fractions;
   (f) determining the amount of asphaltenes in each of said plurality of prior petroleum fraction;
   (g) calculating the ratio of total aromatics to asphaltenes for each of said prior petroleum fractions from the amounts determined in steps (e) and (f);
   (h) determining the tendency of each of said prior petroleum fractions to foul exposed heated metal surfaces; and
   (i) correlating the ratio of step (g) with the corresponding tendency to foul exposed heated metal surfaces of step (h) for each of said prior petroleum fractions.

8. The method of claim 7 wherein said correlating step (i) comprises obtaining a plot of the ratio of step (g) versus the corresponding tendency to foul exposed heated metal surfaces of step (h) for each of said prior petroleum fractions.

9. The method of claim 8 wherein the comparing of step (d) comprises comparing the ratio of step (c) with said plot.

10. The method according to claim 1 wherein the determination of asphaltenes comprises contacting said sample petroleum fraction with an insolubiilizing amount of an antisolvent for asphaltenes, and recovering asphaltenes.

11. The method according to claim 10 wherein said antisolvent is selected from the group consisting of lower paraffinic or polar solvents.

12. The method accoridng to claim 11 wherein said antisolvent is a $C_3$ to $C_{20}$ paraffin.

13. The method according to claim 12 wherein said antisolvent is n-heptane.

14. A method for determining the tendency of a sample petroleum fraction to foul exposed heated metal surfaces comprising:
   (a) determine the amount of total aromatics in said sample petroleum fraction;
   (b) determining the amount of asphatlenes in said sample petroleum fraction;
   (c) calculating the ratio of total aromatics in said sample petroleum fraction to asphaltenes in said sample petroleum fraction form the amounts determined in steps (a) and (b), said ratio providing an indication of the tendency of said sample petroleum fraction to foul exposed heated metal surfaces; and
   (d) determining the tendency of said sample petroleum fraction to foul exposed heated metal surfaces form the ratio of step (c), wherein a low ratio indicates a greater tendency of said sample petroleum fraction to foul exposed heated metal surfaces than a higher ratio.

15. The method according to claim 14 wherein the determining step (d) includes comparing the ratio of step (c) with a standard.

* * * * *